United States Patent [19]

Fenn et al.

[11] 4,311,479
[45] Jan. 19, 1982

[54] METHOD OF INDICATING THE PRESENCE OF AN IMPREGNANT IN A SUBSTRATE

[75] Inventors: David J. Fenn, London; Adrian N. Fellows, Ramsbottom, both of England

[73] Assignee: Exterma-Germ Products Ltd., London, England

[21] Appl. No.: 162,155

[22] Filed: Jun. 23, 1980

Related U.S. Application Data

[63] Continuation of Ser. No. 944,621, Sep. 21, 1978, abandoned.

[51] Int. Cl.$^3$ .......................... D06P 5/00; A61L 2/18; D06P 5/13
[52] U.S. Cl. .......................... 8/495; 8/490; 15/104.93; 424/26; 424/25
[58] Field of Search .......................... 8/490, 403, 495; 15/104.93; 424/26, 25

[56] References Cited

U.S. PATENT DOCUMENTS

| | | | |
|---|---|---|---|
| 805,560 | 11/1905 | Kohn | 424/7 |
| 1,933,302 | 10/1933 | Aurand | 422/8 |
| 2,449,274 | 9/1948 | Broll | 424/7 |
| 2,702,780 | 2/1955 | Lerner | 424/25 |
| 3,530,030 | 9/1970 | Adams et al. | 15/104.93 |
| 3,536,437 | 10/1970 | Rogovin | 8/490 |
| 3,663,262 | 5/1972 | Cogan | 8/403 |
| 3,987,797 | 10/1976 | Stephenson | 424/26 |

*Primary Examiner*—Maria Parrish Tungol
*Attorney, Agent, or Firm*—Frank P. Cyr

[57] ABSTRACT

The invention is a method of indicating the presence of an impregnant, e.g. an antimicrobial composition, in cloth to provide visual evidence of the continuing activity of the impregnant. The antimicrobial composition in the cloth is activated on contact with a liquid such as water and is ionically bonded to the cloth. Small portions of the impregnated cloth are dyed with an indicator dye which bonds preferentially to the antimicrobial composition so that when the antimicrobial composition is exhausted, the dye will disappear from the cloth. The dye is preferably applied to the cloth in stripes.

19 Claims, No Drawings

METHOD OF INDICATING THE PRESENCE OF AN IMPREGNANT IN A SUBSTRATE

This application is a continuation of Application Ser. No. 944,621, filed Sept. 21, 1978, now abandoned.

The invention relates to a method of indicating the presence of an impregnant in a substrate and more particularly, but not exclusively, to a method of indicating the presence of an antimicrobial compound impregnated into a substrate. The term "substrate" used in the specification and claims is intended to include cloth paper and other non-woven materials as well as woven or knitted textile fabrics. Futhermore "substrate" is intended to cover naturally occurring materials such as animal skins.

It is well known that cloths, towels and the like used for wiping soiled surfaces or drying potentially contaminated surfaces present a hygiene hazard in that with repeated use they may cause, by virtue of themselves becoming increasingly contaminated, the spread of harmful active or potentially active micro organisms.

It is known to provide a wiping cloth typically of a viscose non-woven fibre material impregnated with an antimicrobial compound, which may be used for wiping and drying surfaces and by the use of which the spread of active micro organisms is at least reduced causing less risk to public health, the antimicrobial activity of such a cloth being released on contact of the cloth with a polar liquid, such as water. A major disadvantage of the known cloth is that it is impossible to predict when the useful antibacterial life of the impregnated cloth has come to an end. This disadvantage is, of course, true of the use of disinfectants generally.

It is an object of the invention to mitigate this disadvantage.

According to the invention there is provided a substrate impregnated with an agent, at least in part ionically bonded to the substrate, which agent is activated by contact with a polar liquid, a portion of the impregnated substrate having applied thereto a dye of a kind which will bond ionically to the impregnant substantially more than to the substrate. The impregnant may be a deodouriser, a corrosion-inhibitor, an antimicrobial compound or the like. That a suitable substrate-impregnant-dye system has been selected can be verified by a simple procedure. A length of suitable unimpregnated substrate is impregnated in longitudinal stripes with a proposed impregnant. After drying where necessary, the stripe impregnated substrate is dyed all over by immersion in a suitable dye bath. The dyed substrate is then flushed with a large quantity of water and a suitably selected system will be seen to retain the dye substantially only on the impregnated stripes.

Preferably the impregnant is uniformly dispersed over the substrate, and preferably the dye is applied to the substrate in stripes. It is however possible to apply the dye to the substrate in other configurations such as dots.

This in one embodiment the invention provides cloth having visual indication of the presence of an antimicrobial compound impregnated therein, the cloth consisting of a mechanically strong viscose non-woven substrate, the antimicrobial compound being cationic and at least in part ionically bonded to the substrate and possessing bactericidal properties on contact with a polar liquid, the impregnated substrate having an anionic dye applied to a portion thereof so that it bonds ionically to the impregnant but not to the cloth and so that a significant portion of the impregnated fabric remains undyed, as it will probably be that the active property of the impregnant will be adversely affected by reaction and combination with the dye.

From another aspect the invention provides an article comprising cloth as defined above, e.g. disposible clothing such as underwear, combat uniforms or surgeons' gowns or foot mats e.g. for preventing the spread of infection in public swimming baths or disposable bedding. The cloth substrate is preferably of cellulosic material such as natural cellulose, viscose, esterified viscose or oxycellulose since such materials are useful in forming textile cloth of many different kinds and also bond well to cationic anti-microbial compounds. However, many polymeric materials, while in general being less hydrophilic than cellulosic materials or even hydrophobic nevertheless bond to cationic anti-microbial compounds and are appropriate in some circumstances to form cloth substrates. Suitable polymers include polyamides, polyesters, polyacrylonitriles, polyvinylalcohol, polyvinylacetate, polypropylene, polyethylene and polyurethane. Furthermore naturally occurring materials such as wool and animal skins might be suitable substrates.

The antimicrobial compound may be selected from those groups which are soluble in water and exhibit cationic character in their aqueous solutions. Suitable groups include quaternary ammonium compounds, bisguanides, antimicrobial amphoteric surfactants, and mixtures thereof. Examples of suitable quaternary ammonium compounds are alkyl dimethyl benzyl ammonium chlorides e.g. alkyl dimethyl ethyl-benzyl ammonium chloride, and benzalkonium chloride. Alternatively the quaternary ammonium compound may be an alkyl trimethyl ammonium bromide, cetyl pyridinium chloride, or benzethonium chloride. Suitable alkyl groups in such compounds contain predominantly strait chain $C_{12}$ to $C_{18}$ groups. An example of a suitable bisguanide is a soluble salt of 1,6-di-(4-chloro-phenyldisguanido hexane) or a polymeric bisguanide such as Vantocil. (Registered Trade Mark). An example of a suitable amphoteric surfactant is dodecyl-di-(aminoethyl) glycine.

Examples of preferred antimicrobial compounds for use in the present invention are:
(a) A 1:1 mixture of ADBAC (alkyl dimethyl benzyl ammonium chloride) and CTAB (cetyl trimethyl ammonium bromide) dissolved in water and isopropanol to 50% active concentration and applied to the cloth in a further dilution of 1 part composition in 5 parts of water.
(b) Similarly a 1:1 mixture of CTAB and chlorhexidine gluconate (the gluconate salt of 1,6-di-(4-chlorophenyldiguanido hexane).
(c) Similarly a 1:1 mixture of ADBAC and a polymeric bisguanide (such as that sold by I.C.I. under the trade name Vantocil).
(d) Similarly a 5:2 mixture of ADBAC and Vantocil dissolved in water to 35% activity.
(e) Similarly a mixture of 30 parts by weight CTAB dissolved in 100 parts by weight of a 20% aqueous solution of polymeric bisguanide (Vantocil).

The substrate may be impregnated with the antimicrobial compound or mixture of compounds in any convenient way. Thus for example the antimicrobial compound may be dissolved or dispersed in a suitable liquid vehicle, preferably water, and the solution or dispersion applied to the substrate, for example by dipping or spraying. After such treatment the substrate may, if necessary, be dried to the extent that it is dry to the touch, and may undergo such secondary converting operations as are appropriate to the desired end function, e.g. slitting, cutting, folding, making up into garments, etc. if the substrate is woven cloth as an alternative, the impregnant might be incorporated in the yarn from which the cloth is to be woven, before weaving.

That the cloth has been suitably impregnated with an antimicrobial compound and that the impregnant is effectively released to perform its function is readily ascertained by a zone of inhibition test such as the relevant AATCC procedure or a similar variation. A typical result obtained showed that cloth impregnated in accordance with the present invention performed as follows:

| Cloth | Impregnation level of the mixture of Example (e) | Effectiveness as shown by zone of inhibition (Diameter in mm) |
|---|---|---|
| 50 grammes per square meter non-woven textile fabric comprising 51% viscose rayon 20% cellulose pulp and 29% acrylic binder. | 9300 ppm | (a) *Staph aureus* 25 mm (b) *E coli* 6 mm. |

The cloth which has been impregnated more or less uniformly with an effective antimicrobial compound is then dyed over a portion of its surface area with a suitable dye, i.e. a dye which bonds preferentially to the impregnant but does not form a significant bond with the unimpregnated cloth, such that it is an important characteristic of the overall system that the dye, and or any dye-antimicrobial combination present is released (on contact with a polar liquid) at least as quickly and preferably somewhat more rapidly than impregnant which is not in combination with the dye, thereby serving as an indicator of the longevity of the effective antimicrobial life of the impregnated cloth. That such an indication system is effective may readily be discerned by performing zone of inhibition tests during the working life of the cloth, particularly just before and just after disappearance of the indicator colour.

In a preferred embodiment of the invention, the indicator system takes the form of thin stripes, and the disappearance of these stripes during use either as a result of rinsing, soaking, wiping or contact with incompatible materials serves to give an indication of the antimicrobial end-point of the product.

Suitable dyes would be water soluble dyes of substantially anionic character in solution. As the wiping cloth which is a preferred embodiment of this invention is largely intended for use in food related areas, preferred dyes are those which are deemed safe as food additives.

Exemplary dyes are as follows:

| Dye | B.S. Number | E.E.C. Number | F D & C Number | Colour index Number |
|---|---|---|---|---|
| Sunset Yellow FC | 3340 | 110 | Yellow 6 | 15985 |
| Blue X | 4143 | 132 | Blue 2 | 73015 |
| Blue FCF | — | — | Blue 1 | 42090 |
| Green S | 4153 | 142 | — | 44090 |
| Amaranth | 3341 | 123 | Red 2 | 16185 |

-continued

| Dye | B.S. Number | E.E.C. Number | F D & C Number | Colour index Number |
|---|---|---|---|---|
| Violet BNP | — | — | — | — |
| Ponceau 4R | 3342 | 124 | — | 16255 |
| Carmoisine | 3343 | 122 | — | 14720 |
| Geranine 2G | 3611 | — | — | 18050 |

Ancillary material, e.g. preservatives such as benzoic acid may be added to the dye or dye mixture if desired.

It is claimed:

1. An article consisting of a substrate impregnated with an agent, said agent at least in part being ionically bonded to the substrate and released by contact with a polar liquid, a portion of said impregnated substrate having applied thereto a dye of a kind which will bond ionically to the impregnant more than to the substrate, whereby the disappearance of the dye from the substrate during use thereof will indicate to the user the diminution of the impregnant in the substrate.

2. An article according to claim 1, in which the impregnant is uniformly dispersed over the substrate.

3. An article according to claim 1, in which the dye is applied to the substrate in stripes.

4. An article according to claim 1, in which the agent exhibits cationic character when in aqueous solution.

5. An article according to claim 1, wherein the substrate is of cellulosic material.

6. An article according to claim 5, wherein the cellulosic material is fibrous.

7. An article according to claim 5, wherein the substrate is non woven.

8. An article in accordance with claim 1 wherein the substrate is an animal skin.

9. An article in accordance with claim 1 wherein the substrate is cloth.

10. An article in accordance with claim 1 wherein the substrate is paper.

11. A substrate impregnated with a composition at least in part ionically bonded to the substrate, and released by contact with a polar liquid, a portion of said impregnated substrate having applied thereto a dye of a kind which will bond ionically to the impregnant more than to the substrate, said composition exhibiting cationic character when in aqueous solution, said composition is selected from the group consisting of quaternary ammonium compounds, bisguanides, antimicrobial ampohteric surfactants, and mixtures thereof.

12. A substrate according to claim 11, wherein the quaternary ammonium compound is an alkyl dimethyl benzyl ammonium chloride.

13. A substrate according to claim 11, wherein the quaternary ammonium compound is benzalkonium chloride.

14. A substrate according to claim 13, wherein the alkyl group in the quaternary ammonium compound is a straight chain group predominantly in the range $C_{12}$ to $C_{18}$.

15. A substrate according to claim 11, wherein the quaternary ammonium compound is a member of the group consisting of alkyl dimethyl ethyl-benzyl ammonium chloride, alkyl trimethyl ammonium bromide, cetyl pyridinium chloride and benzethonium chloride.

16. A substrate according to claim 11 wherein the bisguanide is a soluble salt of 1,6-di-(4-chloro-phenyl-diguanido hexane).

17. A substrate according to claim 11, wherein the bisguanide is a polymeric bisguanide.

18. A substrate according to claim 11, wherein the amphoteric surfactant is dodecyl-di-(aminoethyl) glycine.

19. A wiping cloth having visual indication of antimicrobial activity comprising a non-woven fibrous viscose substrate impregnated with a mixture comprising 30 parts by weight cetyl trimethyl ammonium bromide dissolved in 100 parts by weight of a 20% aqueous solution of polymeric bisguanide, the impregnant being at least in part ionically bonded to the substrate and being activated on contact with a polar liquid, the impregnated substrate having lines of an anionic dye applied thereto such that the dye bonds ionically to the impregnant substantially more than to the substrate.

* * * * *

UNITED STATES PATENT AND TRADEMARK OFFICE
CERTIFICATE OF CORRECTION

PATENT NO. : 4,311,479

DATED : January 19, 1982

INVENTOR(S) : David J. Fenn et al

It is certified that error appears in the above-identified patent and that said Letters Patent is hereby corrected as shown below:

On the title page, add:

--[30]    Foreign Application Priority Data

Sept. 27, 1977 [GB]  United Kingdon ............40216/77--

Signed and Sealed this

Eleventh Day of December, 1990

Attest:

HARRY F. MANBECK, JR.

Attesting Officer

Commissioner of Patents and Trademarks